US00PP17451P2

(12) United States Plant Patent
Smith

(10) Patent No.: US PP17,451 P2
(45) Date of Patent: Feb. 27, 2007

(54) ***CHRYSANTHEMUM* PLANT NAMED 'ELEGANT YOMARJORIE'**

(50) Latin Name: *Chrysanthemum×morifolium*
Varietal Denomination: Elegant Yomarjorie

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 28 days.

(21) Appl. No.: 11/157,279

(22) Filed: Jun. 21, 2005

(51) Int. Cl.
*A01H 5/00* (2006.01)

(52) U.S. Cl. ..... Plt./287

(58) Field of Classification Search ..... Plt./287
See application file for complete search history.

*Primary Examiner*—Anne Marie Grunberg
*Assistant Examiner*—S. B. McCormick
(74) *Attorney, Agent, or Firm*—C. A. Whealy

(57) ABSTRACT

A new and distinct cultivar of *Chrysanthemum* plant named 'Elegant Yomarjorie', characterized by its upright and somewhat outwardly spreading plant habit; dense and full plant habit; uniform and freely flowering habit; duplex-type inflorescences with elongated oblong-shaped ray florets; dark coral red-colored ray florets; and natural season flowering in early October in the Northern Hemisphere.

2 Drawing Sheets

Botanical designation: *Chrysanthemum×morifolium.*
Cultivar denominaton: 'Elegent Yomarjorie'.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Elegant Yomarjorie'.

The new cultivar is a product of a planned breeding program conducted by the Inventor in Alva, Fla. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Yomarjorie, disclosed in U.S. Plant Pat. No. 13,820. The new *Chrysanthemum* was discovered and selected by the Inventor as a single flowering plant from within a population of plants of the cultivar Yomarjorie in a controlled environment in Alva, Fla. in April, 2002. The selection of this plant was based on its desirable inflorescence form, attractive ray floret color and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Elegant Yomarjorie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Elegant Yomarjorie'. These characteristics in combination distinguish 'Elegant Yomarjorie' as a new and distinct cultivar:

1. Upright and somewhat outwardly spreading plant habit.
2. Freely branching habit; dense and full plants.
3. Uniform and freely flowering habit.
4. Duplex-type inflorescences with elongated oblong-shaped ray florets.
5. Dark coral red-colored ray florets.
6. Natural season flowering in early October in the Northern Hemisphere.

In side-by-side comparisons conducted in Alva, Fla., plants of the new *Chrysanthemum* differed from plants of the parent, the cultivar Yomarjorie, primarily in ray floret coloration as plants of the cultivar Yomarjorie had purple-colored ray florets. In addition, plants of the new *Chrysanthemum* flowered about six days later than plants of the cultivar Yomarjorie when grown under natural season conditions.

Plants of the new *Chrysanthemum* can be compared to plants of the *Chrysanthemum* cultivar Zesty Yovanessa, disclosed in U.S. Plant Pat. No. 16,537. In side-by-side comparisons conducted in Alva, Fla., plants of the new *Chrysanthemum* differed from plants of the cultivar Zesty Yovanessa in the following characteristics:

1. Plants of the new *Chrysanthemum* were smaller than plants of the cultivar Zesty Yovanessa.
2. Plants of the new *Chrysanthemum* flowered about three days later than plants of the cultivar Zesty Yovanessa when grown under natural season conditions.
3. Plants of the new *Chrysanthemum* had smaller inflorescences than plants of the cultivar Zesty Yovanessa.
4. Inflorescences of plants of the new *Chrysanthemum* had darker colored ray florets and more disc florets than inflorescences of plants of the cultivar Zesty Yovanessa.

Plants of the new *Chrysanthemum* can also be compared to plants of the *Chrysanthemum* cultivar Gedi One Gal, disclosed in U.S. Plant Pat. No. 13,807. In side-by-side comparisons conducted in Alva, Fla., plants of the new *Chrysanthemum* differed from plants of the cultivar Gedi One Gal in the following characteristics:

1. Plants of the new *Chrysanthemum* were larger than plants of the cultivar Gedi One Gal.
2. Plants of the new *Chrysanthemum* flowered about one week earlier than plants of the cultivar Gedi One Gal when grown under natural season conditions.
3. Inflorescences of plants of the new *Chrysanthemum* were smaller but more disc florets than inflorescences of plants of the cultivar Gedi One Gal.
4. Ray florets of plants of the new *Chrysanthemum* were more red and retained color better than ray florets of plants of the cultivar Gedi Two Gal.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Elegant Yomarjorie' grown in a container.

The photograph on the second sheet comprises a close-up view of typical inflorescences of the cultivar 'Elegant Yomarjorie'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and early fall in an outdoor nursery under conditions and practices which approximate those generally used in commercial garden-type *Chrysanthemum* production. One cutting was planted in a 15.25-cm container in mid-July, 2004. Plants were grown under natural season conditions. During the production of the plants, temperatures ranged from 10° to 32° C. Measurements and numerical values represent averages for typical flowering plants.

Botanical classification: *Chrysanthemum×morifolium* cultivar Elegant Yomarjorie.

Commercial classification: Duplex-type garden *Chrysanthemum*.

Parentage: Naturally-occurring whole plant mutation of the *Chrysanthemum×morifolium* cultivar Yomarjorie, disclosed in U.S. Plant Pat. No. 13,820.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous duplex-type garden *Chrysanthemum*. Inverted triangle with mounded crown. Stems initially upright, then somewhat outwardly spreading. Freely branching with about nine primary branches with lateral branches potentially forming at every node. Vigorous growth habit.

*Plant height.*—About 29 cm.

*Plant diameter.*—About 45 cm.

*Lateral branches.*—Length: About 26 cm. Diameter: About 7 mm. Internode length: About 2 cm. Aspect: Upright and outwardly spreading. Texture: Pubescent. Color: 146A.

*Foliage description.*—Leaf arrangement: Alternate. Length: About 5.2 cm. Width: About 4.4 cm. Apex: Cuspidate. Base: Mostly truncate. Margin: Palmately lobed, sinuses mostly divergent. Texture, upper surface: Slightly pubescent. Texture, lower surface: Pubescent; veins prominent. Color: Developing foliage, upper surface: Darker green than 147A. Developing foliage, lower surface: More green than 147B. Fully expanded foliage, upper surface: Much darker green than 147A. Developing foliage, lower surface: Close to 147A. Venation, upper surface: Close to 147A. Venation, lower surface: Close to 146A. Petiole length: About 1.7 cm. Petiole diameter: About 3 mm. Petiole color, upper and lower surfaces: Close to 146A.

Inflorescence description:

*Appearance.*—Duplex-type inflorescence form with elongated oblong-shaped ray florets. Inflorescences borne on terminals above foliage, arising from leaf axils. Ray florets developing acropetally on a capitulum. Very freely flowering, about 35 inflorescences per lateral branch.

*Flowering response.*—Under natural season conditions, plants flower in early October in the Northern Hemisphere.

*Inflorescence bud (before showing color).*—Height: About 5 mm. Diameter: About 6.5 mm. Shape: Oblate. Color (lower surface of phyllaries): More green than 147A.

*Inflorescence size.*—Diameter: About 2.5 cm. Depth (height): About 1.3 cm. Disc diameter: About 4 mm; conspicuous. Receptacle diameter: About 4 mm.

*Ray florets.*—Shape: Elongated oblong. Length: About 1.25 cm. Width: About 4 mm. Corolla tube length: About 2.5 mm. Corolla tube diameter: About 1 mm. Apex: Mostly obtuse; occasionally cuspidate or emarginate. Margin: Fused. Texture: Smooth, glabrous; satiny. Surface: Concave to flat. Orientation: Initially upright, then perpendicular to the peduncle. Number of ray florets per inflorescence: About 172 in numerous whorls. Color: When opening, upper and lower surfaces: Initially 154C, then 154C with close to 71A and 72A towards the apices. Fully opened, upper surface: Close to 4D overlain with close to 71A and 72A. Fully opened, lower surface: Close to 4D underlain with 71A and 72A.

*Disc florets.*—Shape: Tubular, elongated. Length: About 3.5 mm. Width, apex: About 1.5 mm. Width, base: About 1 mm. Number of disc florets per inflorescence: About 32. Color: Immature: 154B to 154C. Mature: Apex: 9A. Mid-section: 145C. Base: 155D.

*Phyllaries.*—Quantity per inflorescence: About 24. Length: About 6 mm. Width: About 3 mm. Shape: Ligulate. Apex: Acute. Base: Truncate. Margin: Entire. Texture, upper surface: Smooth, waxy.

Texture, lower surface: Pubescent. Color, upper surface: Close to 146A. Color, lower surface: More green than 147A.

*Peduncle.*—Length: First peduncle: About 5.2 cm. Fourth peduncle: About 9.6 cm. Diameter: About 2 mm. Strength: Strong. Aspect: About 45° from vertical. Texture: Pubescent. Color: Close 146A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 5 mm. Style color: Close to 145D. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° to more than 38° C.

It is claimed:

1. A new and distinct cultivar of *Chrysanthemum* plant named 'Elegant Yomarjorie', as illustrated and described.

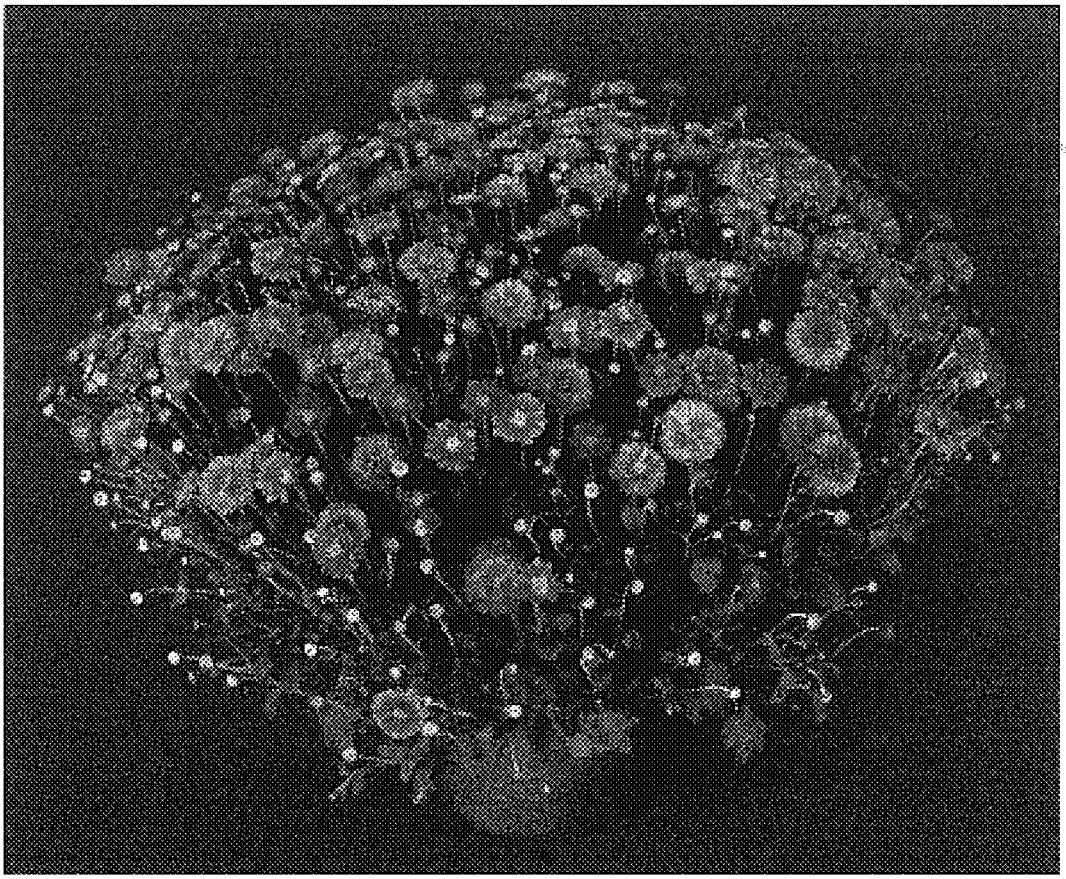

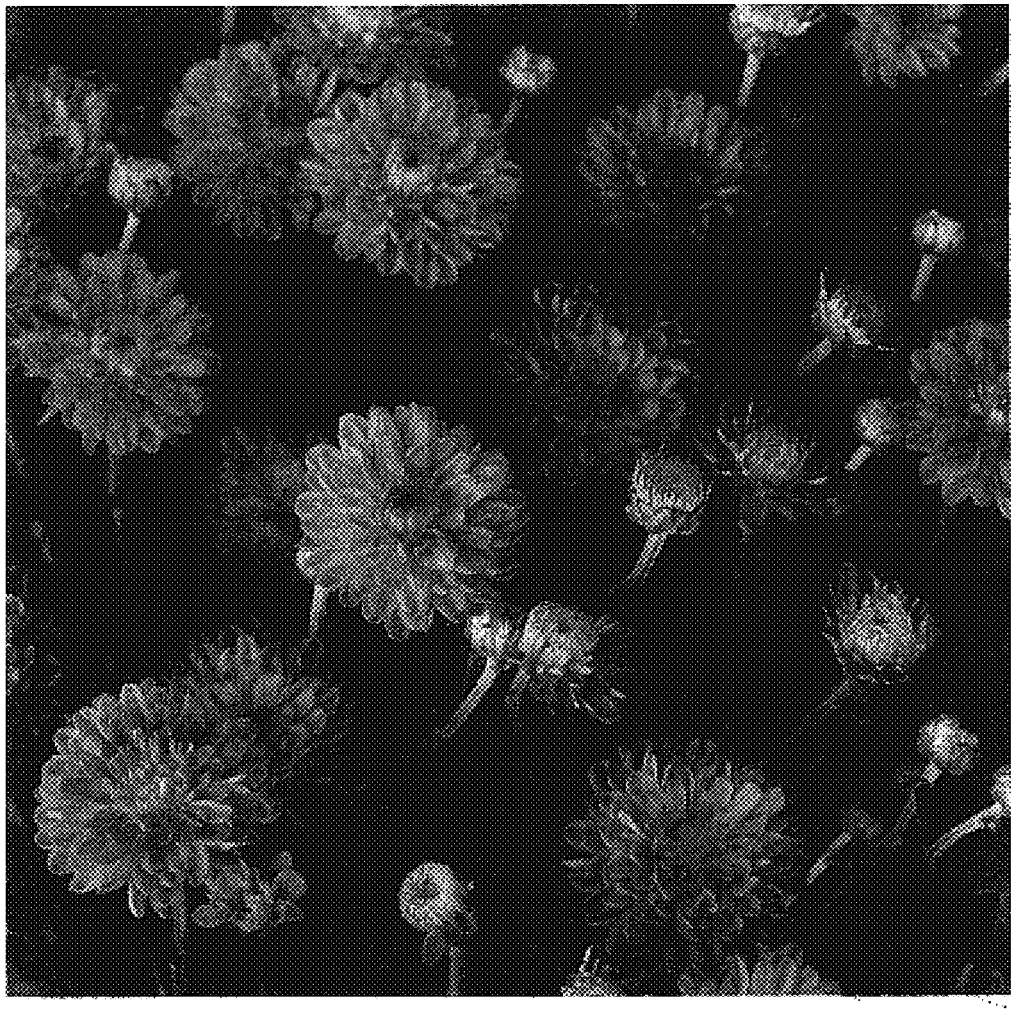

* * * * *